(12) United States Patent  
Parikh et al.

(10) Patent No.: US 11,980,685 B1
(45) Date of Patent: May 14, 2024

(54) LIQUID PHARMACEUTICAL FORMULATIONS OF TAFAMIDIS

(71) Applicant: TaP Pharmaceuticals, AG, Baar (CH)

(72) Inventors: Nilesh Parikh, Irvine, CA (US); William Hite, Winchester, CA (US)

(73) Assignee: TaP Pharmaceuticals, AG, Zug (CH)

( * ) Notice: Subject to any disclaimer, the term of this patent is extended or adjusted under 35 U.S.C. 154(b) by 0 days.

(21) Appl. No.: 18/088,375

(22) Filed: Dec. 23, 2022

(51) Int. Cl.
| | |
|---|---|
| *A61K 9/00* | (2006.01) |
| *A61K 9/08* | (2006.01) |
| *A61K 31/423* | (2006.01) |
| *A61K 47/02* | (2006.01) |
| *A61K 47/26* | (2006.01) |
| *A61K 47/32* | (2006.01) |

(52) U.S. Cl.
CPC .............. *A61K 9/0053* (2013.01); *A61K 9/08* (2013.01); *A61K 31/423* (2013.01); *A61K 47/02* (2013.01); *A61K 47/26* (2013.01); *A61K 47/32* (2013.01)

(58) Field of Classification Search
CPC ...... A61K 9/0053; A61K 9/08; A61K 31/423; A61K 47/02; A61K 47/26; A61K 47/32
See application file for complete search history.

(56) References Cited

U.S. PATENT DOCUMENTS

| 9,770,441 B1 | 9/2017 | Girard et al. |
| 11,208,391 B2 | 12/2021 | Barseghyan et al. |
| 2021/0363116 A1 | 11/2021 | Chen et al. |
| 2022/0251052 A1 * | 8/2022 | Srinivasan ............ C07C 213/08 |
| 2022/0259162 A1 | 8/2022 | Matecic Musanic et al. |

FOREIGN PATENT DOCUMENTS

| WO | 2009027452 A2 | 3/2009 | |
| WO | WO-2011116123 A1 * | 9/2011 | ........... A61K 31/167 |
| WO | 2013168014 A1 | 11/2013 | |
| WO | 2021001858 A1 | 1/2021 | |
| WO | 2021019448 A1 | 4/2021 | |
| WO | 2022084790 A1 | 4/2022 | |
| WO | 2021152623 A1 | 8/2022 | |

OTHER PUBLICATIONS

Pfizer Labs, "Highlights of Prescribing Information Vyndamax and Vyndaqel", Issued May 2019, 16 pages.

* cited by examiner

*Primary Examiner* — Robert A Wax
*Assistant Examiner* — Quanglong N Truong
(74) *Attorney, Agent, or Firm* — John Burr

(57) ABSTRACT

Certain embodiments of the present disclosure provide liquid pharmaceutical formulations, suitable for oral administration, that contain an amount of a tafamidis of from 0.5 mg/ml to 20 mg/ml, water, and an amount of an alkaline pH modifier that yields a content of the tafamidis solubilized in the water of from 0.5 mg/ml to 19.8 mg/ml.

16 Claims, No Drawings

LIQUID PHARMACEUTICAL FORMULATIONS OF TAFAMIDIS

FIELD

The instant disclosure provides pharmaceutical formulations, suitable for oral administration, that are free-flowing aqueous solutions comprising high concentrations tafamidis not previously achievable, and methods of making and using same.

BACKGROUND

Tafamidis is a selective stabilizer of transthyretin. Tafamidis acid has an empirical formula of $C_{14}H_7C_{12}NO_3$, a molecular weight of 308.12 g/mol, and a structural formula of:

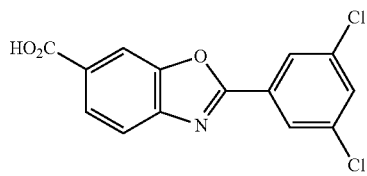 [SMILES: O=C(O)c1ccc2nc(-c3cc(Cl)cc(Cl)c3)oc2c1]

Tafamidis is also known by its IUPAC name 2-(3,5-dichlorophenyl)-1,3-benzoxazole-6-carboxylic acid, and by its CAS Registry Number 594839-88-0. It is the main active pharmaceutical ingredient in a commercial formulation of crystalline 2-(3,5-dichlorophenyl)-1,3-benzoxazole-6-carboxylic acid encapsulated in a soft gel capsule provided under the trade name VYNDAMAX® and indicated for the treatment of the cardiomyopathy of wild-type or hereditary transthyretin-mediated amyloidosis in adults to reduce cardiovascular mortality and cardiovascular-related hospitalization.

United States Patent Application Publication No. 2021/0363'116 (the "'116 publication") discloses crystalline forms of tafamidis. The '116 publication states that U.S. Pat. No. 9,770,441 (the "441 patent") teaches tafamidis forms 1, 2, 4, and 6, of which form 2 is a tetrahydrofuran solvate and forms 4 and 6 are unstable, such that forms 2,4, and 6 are unsuitable for drug development. The '116 publication asserts that tafamidis form 1 of the '441 patent is more stable than forms 2, 4, and 6, but has low solubility. The '116 publication further states that U.S. patent Ser. No. 11/208,391 discloses a crystalline, acetic acid solvate form tafamidis, which was found unstable in drug product. The '116 publication states that, to overcome disadvantages of the prior art, it provides fumaric acid, glutaric acid, and adipic acid co-crystals of tafamidis. In particular, those tafamidis co-crystals have good stability, high solubility, low hygroscopicity, high dissolution, which solve the problems in the prior arts and are of great significance for the development of drugs containing tafamidis.

In its Example 6, the '116 publication discloses side-by-side comparative experiments of the solubility of its tafamidis-fumaric acid co-crystal with the '441 patent-taught tafamidis crystal form 1 in simulated gastric fluid ("SGF"), fed-state simulated intestinal fluid ("FeSSIF"), and fasted-state simulated intestinal fluid ("FaSSIF"). The '116 publication states that solubility in these media is close to in vivo solubility. It specifies that 20 mg of its tafamidis-fumaric acid co-crystal and 20 mg of '441 patent-taught tafamidis crystal form 1 were suspended into 3.0 mL of SGF, 3.0 mL of FeSSIF, and 3.0 mL of FaSSIF to get saturated solutions. After equilibrated for 1 h, concentrations (μg/mL) of tafamidis in the saturated solutions were measured by ultra-high performance liquid chromatography. The results are listed in Table A, which reproduces the '116 publication's Table 7:

TABLE A

| Medium | '116 publication's tafamidis-fumaric acid co-crystal | '441 patent's tafamidis crystal form 1 |
|---|---|---|
| SGF | 5.6 μg/mL | 1.5 μg/mL |
| FeSSIF | 6.0 μg/mL | 0.6 μg/mL |
| FaSSIF | 11.5 μg/mL | 9.0 μg/mL |

In its Example 12, the '116 publication discloses side-by-side comparative experiments for the dissolution profiles of tafamidis formulations filled into 0 #gelatin capsules. The formulations are disclosed in Tables B and C below, which reproduces the '116 publication's Tables 13 and 14:

TABLE B

| Component | mg/unit | % w/w | Function |
|---|---|---|---|
| Tafamidis-fumaric acid co-crystal | 72.5 | 12.08 | API co-crystal |
| PEG 400 | 390.8 | 65.13 | Diluent |
| Fumaric acid | 16.1 | 2.68 | Stabilizer |
| Povidone K30 | 20.0 | 3.33 | Suspending agent |
| Dibutylhydroxytoluene | 0.6 | 0.1 | Antioxidant |
| Polysorbate 80 | 100 | 16.67 | Surfactant |
| Total | 600 | 100 | |

Note:
72.5 mg of tafamidis-fumaric acid co-crystal is equivalent to 61 mg of tafamidis.

TABLE C

| Component | mg/unit | % w/w | Function |
|---|---|---|---|
| '441 patent's tafamidis crystal form 1 | 61 | 10.17 | API |
| PEG 400 | 402.3 | 67.05 | Diluent |
| Fumaric acid | 16.1 | 2.68 | Stabilizer |
| Povidone K30 | 20.0 | 3.33 | Suspending agent |
| Dibutylhydroxytoluene | 0.6 | 0.1 | Antioxidant |
| Polysorbate 80 | 100 | 16.67 | Surfactant |
| Total | 600 | 100 | |

Tables D and E below are the '116 publication's disclosure, in its Tables 15 and 16, of dissolution experimental conditions and results for the tafamidis formulations set forth in above Tables B and C.

TABLE D

| Equipment | Sotax AT7 |
|---|---|
| Method | Paddle |
| Dose | 61 mg |
| Volume | 900 ml |
| Speed | 50 RPM |
| Temperature | 37° C. |
| Sampling point | pH 6.8 PBS: 0, 5, 10, 15, 20, 30, 45, 60 min |
| Media replenishment | No |

TABLE E

| Time (min) | Cumulative drug release (%) | |
|---|---|---|
| | '441 patent's tafamidis crystal form 1 | '116 publication's tafamidis-fumaric acid co-crystal |
| 0 | 0.0 | 0.0 |
| 5 | 14.0 | 6.6 |
| 10 | 27.3 | 67.6 |
| 15 | 29.1 | 82.8 |
| 20 | 28.1 | 88.4 |
| 30 | 27.6 | 89.1 |
| 45 | 26.8 | 87.4 |
| 60 | 21.8 | 86.4 |

The Canadian Product Monograph for VYNDAMAX tafamidis capsules 61 mg reports the aqueous solubility of tafamidis as a function of pH, as shown in Table F. Chapter VII of the Product Quality Review for New Drug Application 212161 ("NDA 212161"), underlying VYNDAMAX, by the Center for Drug Evaluation and Research of the United States Food and Drug Administration, also contains Table F. With respect to Table F, the applicant for NDA 212161 states it "indicate[s] that tafamidis is a poorly soluble drug substance, per the BCS criteria, and exhibits pH independent solubility/insolubility in the pH range of [redacted] and increased solubility at a higher pH."

TABLE F

Aqueous Solubility of Tafamidis

| Water | pH | Solubility (mg/ml) |
|---|---|---|
| 0.02M Acetate-phosphate buffer | 7.6 | 0.0175 |
| 0.02M Acetate-phosphate buffer | 2.6 | <0.002 |
| 0.02M Acetate-phosphate buffer | 5.3 | <0.002 |
| 0.02M Acetate-phosphate buffer | 6.3 | 0.002 |
| 0.02M Acetate-phosphate buffer | 7.0 | 0.0158 |
| 0.02M Acetate-phosphate buffer | 7.8 | 0.0728 |
| 0.02M Acetate-phosphate buffer | 8.0 | 0.140 |

SUMMARY

Embodiments of the present disclosure provide liquid pharmaceutical formulations, suitable for oral administration, that contain an amount of tafamidis of from 0.5 mg/ml to 20 mg/ml; water; and an amount of an alkaline pH modifier sufficient to yield a content of the tafamidis that is dissolved in the water of from 0.5 mg/ml to 19.8 mg/ml. Such formulations can have a pH of from 6 to 11. Some such formulations can further contain one or more of (i) from 5 mg/ml to 50 mg/ml of a polyvinylpyrrolidone (PVP) having a K value of from 10 to 120; (ii) from 50 mg/ml to 500 mg/ml of a polysorbate 20, a polysorbate 40, a polysorbate 60, a polysorbate 80, or a combination thereof of, and (iii) an amount of an acidic pH adjuster sufficient to yield a pH of the formulation of from 6 to 10. In some of such formulations, the alkaline pH modifier is sodium carbonate, potassium carbonate, calcium carbonate, magnesium carbonate, ammonium carbonate, sodium bicarbonate, potassium bicarbonate, calcium bicarbonate, magnesium bicarbonate, ammonium bicarbonate, sodium citrate, potassium citrate, calcium citrate, sodium hydroxide, potassium hydroxide, calcium hydroxide, magnesium hydroxide, ammonium hydroxide, sodium phosphate, potassium phosphate, calcium phosphate, magnesium phosphate, sodium oxide, potassium oxide, calcium oxide, magnesium oxide, ammonium phosphate, ammonia, tromethamine, or a combination of at least any two thereof. In some of such formulations, the formulations contain two or more of (i), (ii), and (iii) or each of (i), (ii), and (iii). In some of such formulations, the PVP is PVP K30 and the polysorbate is the polysorbate 20. In some of such formulations, the alkaline pH modifier is the sodium carbonate, the sodium hydroxide, the potassium hydroxide, the tromethamine or a combination of at least any two thereof and the acidic pH adjuster is hydrochloric acid, hydrofluoric acid, sulfuric acid, chromic acid, nitric, and phosphoric acid, or a combination of at least any two thereof. In some of such formulations, the content of the tafamidis that is dissolved in the water is from 5 mg/ml to 15 mg/ml. In some of such formulations, the formulations are free of added polyethylene glycol and wherein the formulation is free of added glycerol.

Embodiments of the present disclosure provide methods of treating cardiomyopathy or peripheral neuropathy arising from transthyretin amyloidosis, comprising orally administering the liquid formulation of claim 1 to a subject presenting cardiomyopathy or peripheral neuropathy arising from transthyretin amyloidosis. In some of such methods, the formulations are administered to the subject once daily and wherein the liquid formulation comprises from 10 mg to 80 mg tafamidis.

Embodiments of the present disclosure provide liquid pharmaceutical formulations, suitable for oral administration, that contain: from 10 mg/ml to 15 mg/ml of a tafamidis; water; an amount of an alkaline pH modifier that is from 5 mg/ml to 10 mg/ml and that is sufficient to yield a content of the tafamidis that is dissolved in the water of from 10 mg/ml to 12.5 mg/ml, wherein the alkaline pH modifier is sodium carbonate, sodium hydroxide, potassium hydroxide, tromethamine, or a combination thereof; from 30 mg/ml to 35 mg/ml of a PVP K30; from 10 mg/ml to 15 mg/ml of a polysorbate 20; and an amount of and acidic pH adjuster that is sufficient to adjust the pH of the formulation to from about pH 6 to about pH 10, wherein the acidic pH adjuster is hydrochloric acid, hydrofluoric acid, sulfuric acid, chromic acid, nitric, and phosphoric acid, or a combination of at least any two thereof. Some of such formulations are free of both: (i) added polyethylene glycol, and (ii) glycerol.

Embodiments of the present disclosure provide formulations, suitable for oral administration, that contain: about 12.2 mg/ml of a tafamidis; about 8.3 mg/ml of a sodium carbonate; about 33.1 mg/ml of a PVP K30; about 11.2 mg/ml of a polysorbate 20; an amount of hydrochloric acid sufficient to adjust the pH of the formulation to from about pH 6 to about pH 10; and water, wherein a percentage of the tafamidis in the formulation dissolved in the water is from about 75% to about 99%.

Embodiments of the present disclosure provide the use of tafamidis to prepare a liquid medicament for treatment of peripheral neuropathy or cardiomyopathy of wild-type or hereditary transthyretin-mediated amyloidosis. In some of such embodiments, the percentage of the tafamidis in the formulation that is dissolved in water is from about 75% to about 99% w/w of the total tafamidis in the formulation. In some of such embodiments, the formulation contains an amount of a tafamidis of about 12.2 mg/ml; an amount of a sodium carbonate of about 8.3 mg/ml; an amount of a PVP K30 of about 33.1 mg/ml; an amount of a polysorbate 20 of about 11.2 mg/ml; an amount of HCl sufficient to adjust the pH of the formulation to from about pH 6 to about pH 9; and water. In such embodiments, a percentage of the dissolved tafamidis in the formulation is from about 75% to about 99%. In some of such embodiments, the formulations are free of both: (i) added polyethylene glycol, and (ii) glycerol.

The total amount of tafamidis in some formulations administered to a subject, of the present disclosure is 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, or ranges therebetween.

DETAILED DESCRIPTION

The present disclosure provides aqueous pharmaceutical formulations, suitable for oral administration, comprising tafamidis (e.g., without limitation, a tafamidis free acid) and an amount of an alkaline pH modifier sufficient to yield a content of the tafamidis that is dissolved in the water of 0.5 mg/ml or more. Such formulations of the disclosure are useful for treating cardiomyopathy of wild-type or hereditary transthyretin-mediated amyloidosis to reduce cardiovascular mortality and cardiovascular-related hospitalization.

One advantage of pharmaceutical formulations as disclosed herein is that they provide unexpectedly high concentrations of tafamidis in solution, and especially in aqueous solution.

Another advantage of pharmaceutical formulations as disclosed herein is that, to the degree that the formulation includes a part of the tafamidis as suspended amorphous particles or crystals, the proportion of the tafamidis that is present in the solution phase is unexpectedly high compared to prior art formulations. In some formulations of the disclosure, the proportion of tafamidis in the solution phase can be from 75% to 99%, from 80% to 99%, from 85% to 99%, from 90% to 99%, or from 95% to 99%. In some formulations of the disclosure, the proportion of tafamidis in the solution phase can be from 75% to 98%, from 80% to 98%, from 85% to 98%, from 90% to 98%, or from 95% to 98%. In some formulations of the disclosure, the proportion of tafamidis in the solution phase can be from 75% to 97%, from 80% to 97%, from 85% to 97%, from 90% to 97%, or from 95% to 97%.

Formulations as disclosed herein can "comprise" a list of ingredients, such list then being open to inclusion of further unspecified ingredients. Alternatively, formulations as disclosed herein can "consist of" a list of ingredients, meaning that the formulations include only the listed ingredients. Or, formulations as disclosed herein can "consist essentially of" the listed ingredients, meaning that the formulations include all of the listed ingredients, and may include as well any further ingredients that do not materially affect the utility of the formulation."

In some embodiments, active pharmaceutical ingredient ("API") in formulations of the present disclosure is a 1,3-benzoxazole carboxylic acid that is substituted at the 2 position by a halophenyl group. The halophenyl group can be mono-halo- or di-halo-substituted. A halogen substituent is preferably Cl or F or Br. The carboxylic acid is preferably joined at the 6 position, but can be at any of the 4, 5 or 7 positions as well. The API in the working examples is tafamidis, 2-(3,5-dichlorophenyl)-1,3-benzoxazole-6-carboxylic acid, but examples of additional halophenyl 1-3-benoxazole carboxylic acids that might be used are: 2-(3,5-dichlorophenyl)-1,3-benzoxazole-6-carboxylic acid, 2-(3-fluoro,5-chloro)-1,3-benzoxazole-6-carboxylic acid, 2-(3,5-difluoro)-1,3-benzoxazole-6-carboxylic acid, 2-(3,5-dichlorophenyl)-1,3-benzoxazole-5-carboxylic acid, 2-(3-fluoro,5-chloro)-1,3-benzoxazole-5-carboxylic acid, 2-(3,5-difluoro)-1,3-b enzoxazole-5-carboxylic acid, 2-(3,5-dibromophenyl)-1,3-benzoxazole-6-carboxylic acid, 2-(3-bromo,5-chloro)-1,3-b enzoxazole-6-carboxylic acid, 2-(3-bromo,5-fluoro)-1,3-benzoxazole-6-carboxylic acid, 2-(3-fluoro,5-bromo)-1,3-benzoxazole-5-carboxylic acid, 2-(3,5-difluoro)-1,3-benzoxazole-5-carboxylic acid.

In some embodiments, formulations of this disclosure, the API can be provided in the form of a co-crystal together with fumaric acid, glutaric acid or adipic acid. In the working Examples, the API is tafamidis and it is provided in the form of a co-crystal with fumaric acid or as the crystals of the Form 1 described in the '441 patent.

In some embodiments, formulations of the present disclosure contain the API, for example tafamidis, at concentrations, in the overall formulation of from 0.5 mg/ml to 30 mg/ml and exemplary particular concentrations include 0.5 mg/ml, 0.75 mg/ml, 1 mg/ml, 1.25 mg/ml, 1.5 mg/ml, 1.75 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 10.5 mg/ml, 11 mg/ml, 11.5 mg/ml, 12 mg/ml, 12.5 mg/ml, 13 mg/ml, 13.5 mg/ml, 14 mg/ml, 14.5 mg/ml, 15 mg/ml, 15.5 mg/ml, 16 mg/ml, 16.5 mg/ml, 17 mg/ml, 17.5 mg/ml, 18 mg/ml, 18.5 mg/ml, 19 mg/ml, 19.5 mg/ml, or 20 mg/ml, 20.5 mg/ml, 21 mg/ml, 21.5 mg/ml, 22 mg/ml, 22.5 mg/ml, 23 mg/ml, 23.5 mg/ml, 24 mg/ml, 24.5 mg/ml, 25 mg/ml, 25.5 mg/ml, 26 mg/ml, 26.5 mg/ml, 27 mg/ml, 27.5 mg/ml, 28 mg/ml, 28.5 mg/ml, 29 mg/ml, 29.5 mg/ml, or 30 mg/ml as well as ranges between any two of said in API, for example tafamidis, concentrations.

In some embodiments, formulations of the disclosure contain the API, for example tafamidis, in weight to volume proportions, in the overall formulation, of from 0.001% w/v to 25% w/v, and further exemplary proportions of tafamidis include 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, 2.5% w/v, 3% w/v, 4% w/v, 5% w/v, 7.5% w/v, 10% w/v, 12.5% w/v, 15% w/v, 17.5% w/v, 20% w/v, 22.5% w/v, 25% w/v, as well as ranges between any two of said weigh to volume proportions.

In some embodiments, formulations of the present disclosure contain the API, for example tafamidis, at concentrations, in the solution phase of the formulation of from 0.5 mg/ml to 30 mg/ml and exemplary particular concentrations include 0.5 mg/ml, 0.75 mg/ml, 1 mg/ml, 1.25 mg/ml, 1.5 mg/ml, 1.75 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 10.5 mg/ml, 11 mg/ml, 11.5 mg/ml, 12 mg/ml, 12.5 mg/ml, 13 mg/ml, 13.5 mg/ml, 14 mg/ml, 14.5 mg/ml, 15 mg/ml, 15.5 mg/ml, 16 mg/ml, 16.5 mg/ml, 17 mg/ml, 17.5 mg/ml, 18 mg/ml, 18.5 mg/ml, 19 mg/ml, 19.5 mg/ml, or 20 mg/ml, 20.5 mg/ml, 21 mg/ml, 21.5 mg/ml, 22 mg/ml, 22.5 mg/ml, 23 mg/ml, 23.5 mg/ml, 24 mg/ml, 24.5 mg/ml, 25 mg/ml, 25.5 mg/ml, 26 mg/ml, 26.5 mg/ml, 27 mg/ml, 27.5 mg/ml, 28 mg/ml, 28.5 mg/ml, 29 mg/ml, 29.5 mg/ml, or 30 mg/ml as well as ranges between any two of said in API, for example tafamidis, in solution phase concentrations.

In some embodiments, formulations of the disclosure have a proportion of the overall amount of the API, for example tafamidis, present in the formulation that is dissolved in water (i.e., in solution) that is 70%, 75%, 80%, 85%, 90%, 91%, 92%, 93%, 94%, 95%, 96%, 97%, 98%, 99%, 100%, or in a range between any two of such proportions.

In some embodiments, formulations of the present disclosure can contain an alkaline pH modifier. Alkaline pH modifiers useful in the formulations of the present disclosure include sodium carbonate, potassium carbonate, calcium carbonate, magnesium carbonate, ammonium carbonate, sodium bicarbonate, potassium bicarbonate, calcium bicarbonate, magnesium bicarbonate, ammonium bicarbonate, sodium citrate, potassium citrate, calcium citrate, sodium hydroxide, potassium hydroxide, calcium hydroxide, magnesium hydroxide, ammonium hydroxide, sodium phosphate, potassium phosphate, calcium phosphate, magnesium phosphate, sodium oxide, potassium oxide, calcium oxide, magnesium oxide, ammonium phosphate, ammonia, tromethamine, or combinations thereof. In such embodiments, formulations of the disclosure may comprise alkaline pH modifiers in concentrations of from 0.01 mg/ml to 20 mg/ml, and exemplary particular concentrations of alkaline pH modifiers useful in formulations of the disclosure include 0.01 mg/ml, 0.05 mg/ml, 0.5 mg/ml, 0.75 mg/ml, 1 mg/ml, 1.25 mg/ml, 1.5 mg/ml, 1.75 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 10.5 mg/ml, 11 mg/ml, 11.5 mg/ml, 12 mg/ml, 12.5 mg/ml, 13 mg/ml, 13.5 mg/ml, 14 mg/ml, 14.5 mg/ml, 15 mg/ml, 15.5 mg/ml, 16 mg/ml, 16.5 mg/ml, 17 mg/ml, 17.5 mg/ml, 18 mg/ml, 18.5 mg/ml, 19 mg/ml, 19.5 mg/ml, or 20 mg/ml, as well as ranges between any two of said concentrations. The formulations may comprise combinations of alkaline pH modifiers, in amounts that individually or in aggregate achieve(s) the stated concentrations.

In some embodiments, formulations of the disclosure can contain a pH adjusting agent and/or a buffer. Acidic pH adjusting agents useful in formulations of the disclosure include fumaric acid, formic acid, acetic acid, trichloroacetic acid, benzoic acid, oxalic acid, hydrofluoric acid, hydrogen sulfide, nitrous acid, sulfurous acid, phosphoric acid, and combinations thereof. Alkaline pH adjusting useful in formulations of the disclosure include sodium hydroxide, potassium hydroxide, calcium hydroxide, ammonium carbonate, ammonium hydroxide, ethanolamine, and trolamine. Buffers useful in formulations of the disclosure include is acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, a tartaric acid, sodium tartrate, sodium bicarbonate, sodium carbonate, tris(hydroxymethyl)aminomethane ("TRIS"), or a combination thereof. In such formulations, the buffer and/or pH adjusting agent are present in the formulations in amounts, alone or together, that are sufficient to cause the formulation to have a pH of from 6 to 11, for example pH 6, pH 6.1, pH 6.2, pH 6.3, pH 6.4, t pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5, pH 8.6, pH 8.7, pH 8.8, pH 8.9, pH 9, pH 9.1, pH 9.2, pH 9.3, pH 9.4, pH 9.5, pH 9.6, pH 9.7, pH 9.8, pH 9.9, pH 10, pH 9, pH 9.1, pH 9.2, pH 9.3, pH 9.4, pH 9.5, pH 9.6, pH 9.7, pH 9.8, pH 9.9, pH 10, pH 10.1, pH 10.2, pH 10.3, pH 10.4, pH 10.5, pH 10.6, pH 10.7, pH 10.8, pH 10.9, pH 11, as well as in a range between any two such pH values.

In some embodiments, formulations of the present disclosure are pourable. The viscosities of such formulations can range from 1 centipoise ("cps") (i.e., the viscosity of water at room temperature) to 25,000 cps (i.e., the viscosity of chocolate syrup at room temperature); and exemplary particular viscosities of formulations of the disclosure include 1 cps, 25 cps, 50 cps, 75 cps, 100 cps, 150 cps, 200 cps (about the viscosity of maple syrup at room temperature), 250 cps, 300 cps, 400 cps, 500 cps, 600 cps, 700 cps, 800 cps, 900 cps, 1000 cps (about the viscosity of glycerin at room temperature), 1100 cps, 1200 cps, 1300 cps, 1400 cps, 1500 cps, 1600 cps, 1700 cps, 1800 cps, 1900 cps, 2000 cps, 2100 cps, 2200 cps, 2300 cps, 2400 cps, 2500 cps, 2600 cps, 2700 cps, 2800 cps, 2900 cps, 3000, 3500 cps, 4000 cps, 4500 cps, 5000 cps, 6000 cps, 7000 cps, 8000 cps, 9000 cps, 10,000 cps, 12,500 cps, 15,000 cps, 17,500 cps, 20,000, cps 22,500 cps, 25,000 cps (about the viscosity of chocolate syrup at room temperature), 27,500 cps, 30,000, cps as well as in a range between any two of said viscosities.

In some embodiments, formulations of the disclosure can contain a polymer. Non-ionic polymers useful in certain formulations of the disclosure include hydroxyethyl cellulose, hydroxypropylmethyl cellulose, methyl cellulose, carboxymethyl cellulose, polyvinyl pyrrolidone, and polyvinyl alcohol. Ionic polymers useful in certain formulations of the disclosure include polyacrylates (e.g., carbopols and carbomers), alginates, chitosans, hyaluronic acid, and xanthan gum. Such ionic and/or nonionic polymers may be present in formulations of the disclosure in weight to volume proportions of the overall formulation of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, or 5.0% w/v, as well as in a range between any two of said polymer proportions. The formulations may comprise combinations of polymers, in amounts that individually or in aggregate achieve(s) the stated polymer proportions.

In some embodiments, formulations of the disclosure can contain an acidic pH adjuster. Acidic pH adjusters useful in formulations of the disclosure include fumaric acid, formic acid, acetic acid, trichloroacetic acid, benzoic acid, oxalic acid, hydrofluoric acid, hydrogen sulfide, nitrous acid, sulfurous acid, phosphoric acid, and combinations thereof. Such acidic pH adjusters may be present in formulations of the disclosure in sufficient to achieve a pH of 6 to 11, for example pH 6, pH 6.1, pH 6.2, pH 6.3, pH 6.4, t pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5, pH 8.6, pH 8.7, pH 8.8, pH 8.9, pH 9, pH 9.1, pH 9.2, pH 9.3, pH 9.4, pH 9.5, pH 9.6, pH 9.7, pH 9.8, pH 9.9, pH 10, pH 9, pH 9.1, pH 9.2, pH 9.3, pH 9.4, pH 9.5, pH 9.6, pH 9.7, pH 9.8, pH 9.9, pH 10, pH 10.1, pH 10.2, pH 10.3, pH 10.4, pH 10.5, pH 10.6, pH 10.7, pH 10.8, pH 10.9, pH 11, as well as in a range between any two such pH values.

In some embodiments, formulations of the disclosure contain a surfactant. Surfactants useful in certain formulations of the disclosure include sodium lauryl sulfate, docusate sodium, phosphatidylcholine, lecithin, betaines, tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. Such surfactants may be present in formulations of the disclosure in weight to volume proportions of the overall formulation of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or in a ranges between any two of said surfactant proportions. The formulations may comprise combinations of surfactants, in amounts that individually or in aggregate achieve(s) the stated weight to volume proportions.

In some embodiments, formulations of the disclosure can contain a tonicity agent. Ionic tonicity agents useful in certain formulations of the disclosure include calcium chloride, magnesium chloride, potassium chloride, sodium chloride, sodium sulfate, and combinations thereof. Nonionic tonicity agents useful in the formulations described herein include mannitol, sorbitol, xylitol, erythritol, lactitol, maltitol, isomalt, and combinations thereof. The formulations may comprise tonicity agent in weight to volume proportions of the overall formulation of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or in a range between any two of said tonicity agent proportions. The formulations may comprise combinations of tonicity agent, in amounts that individually or in aggregate achieve(s) the stated tonicity weight to volume proportions.

In some embodiments, formulations of the disclosure can include a sweetener. Sweeteners useful in the formulations of the present disclosure include acesulfame-K, advantame, alitame, aspartame, brazzein, carrelame, curculin, cyclamic acid, corn syrup (e.g., high fructose corn syrup), cyclamate, dihydrochalchone, erythritol, fructose, galactose, glucose, glycerin, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, *stevia* glycosides, sucralose, sucrose, tagatose, tryptophan, and xylitol. The sweetener may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said sweetener proportions. The formulations may comprise combinations of sweeteners, in amounts that individually or in aggregate achieve(s) the stated weight to volume proportions.

In some embodiments, formulations of the disclosure can include a flavorant. Flavorants useful in the formulations of the present disclosure include chocolate, vanilla, caramel, orange, lemon, lime, strawberry, raspberry, blueberry, cherry, cinnamon, and nutmeg. The flavorant may be present in liquid pharmaceutical formulations of the disclosure in weight to volume proportions of 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v 0.75% w/v, 0.80% w/v, 80.5% w/v, 0.90% w/v, 0.95% w/v, 1% w/v, 2% w/v, 3% w/v, 4% w/v, 5% w/v, 6% w/v, 7% w/v, 8% w/v, 9% w/v, 10% w/v or in a range between any two of said flavorant proportions. The formulations may comprise combinations of flavorant, in amounts that individually or in aggregate achieve(s) the stated weight to volume proportions.

In some embodiments, formulations of the disclosure can contain a preservative. Preservatives useful in certain formulations of the disclosure include dibutylhydroxytoluene, benzalkonium chloride, benzyl alcohol, borates, parabens, cresols, benzoic acid, phenol, sorbic acid, benzethonium chloride, sodium chlorite and combinations thereof. The formulations may comprise preservative in weight to volume proportions of the overall formulation of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, and 5.0% w/v, or in a range between any two of said preservative proportions. The formulations may comprise combinations of preservatives, in amounts that individually or in aggregate achieve(s) the stated weight to volume proportions.

Examples

Aspects of embodiments of the present disclosure may be further understood in light of the following examples, which should not be construed as limiting in any way. Objectives of the solubility and viscosity studies of the present disclosure were to evaluate the extent of tafamidis solubility and viscosity in a variety of aqueous formulations. Forms of tafamidis studied in these Examples include the tafamidis-fumaric co-crystal according to the '116 publication and tafamidis polymorph form 1 according to the '441 patent.

Example 1

Tafamidis solubility and viscosity studies. Aqueous tafamidis formulations 0263-11A, 0263-11B, 0263-11C, and 0263-11D comprised the ingredients and pH set forth in Table 1.1 and were studied in the solubility and viscosity experimental protocols described in this Example 1.

TABLE 1.1

Tafamidis formulations 0263-11A-D

| Ingredient | 0263-11A | | 0263-11B | | 0263-11C | | 0263-11D | |
|---|---|---|---|---|---|---|---|---|
| | mg/ml | % w/v | mg/ml | % w/v | mg/ml | % w/v | mg/ml | % w/v |
| Tafamidis-fumaric acid co-crystal | 14.4* | 1.4 | 14.4* | 1.4 | 14.4* | 1.4 | 0 | 0 |
| Tafamidis form 1 | 0 | 0 | 0 | 0 | 0 | 0 | 12.2 | 1.22 |
| Purified water | 650 | 6.5 | 650 | 6.5 | 650 | 6.5 | 650 | 6.5 |
| Sodium carbonate | 8.3 | 0.83 | 8.3 | 0.83 | 8.3 | 0.83 | 8.3 | 0.83 |
| Povidone K 30 | 33.1 | 3.31 | 33.1 | 3.31 | 33.1 | 3.31 | 33.1 | 3.31 |
| Polysorbate 20 | 112 | 11.2 | 112 | 11.2 | 112 | 11.2 | 112 | 11.2 |
| 1N HCl | Q.S. to pH 7.5 | | Q.S. to pH 8.0 | | Q.S. to pH 8.5 | | Q.S. to pH 8.0 | |
| Purified water | Q.S. | | Q.S. | | Q.S. | | Q.S. | |

*14.4 mg tafamidis-fumaric acid is equivalent to 12.2 mg tafamidis + 2.2 mg fumaric acid.

Formulations 0263-11A, 0263-11B, 0263-11C, and 0263-11D were made as follows. A bulk master mix solution was made by mixing 32.5 g of purified water and 5.6 g of polysorbate 20 in a 25 ml beaker with a magnetic stir rod. 414 mg of sodium carbonate was then added and mixed until dissolved. 1.655 g of povidone K30 was gradually added and mixed with the magnetic stir bar for at least twenty minutes until dissolved, clear, and free of bubbles. Then 8.034 g of the bulk solution was weighed into a 25 ml scintillation vial and mixed with a magnetic stirring rod while being heated to 50° C. 72 mg of tafamidis-fumaric acid co-crystal or 61 mg of tafamidis polymorph 1 was slowly added and mixed while heating at 50° C. until a clear solution was formed. Then an additional 72 mg of tafamidis-fumaric acid co-crystal acid or 61 mg of tafamidis polymorph form 1 was slowly added with continued mixing at 50° C. until a clear solution was formed. The pH of resulting solutions was measured and adjusted to the pH indicated for each formulation in Table 1.1 using 1N HCl, and then diluted to 10 ml with purified water. Once a clear solution had formed, 5 ml was transferred into a microcentrifuge vial and centrifuged at 5000×g for 2 minutes. All visual solubility and viscosity observations for each of the formulations were then made and recorded. Two samples of each of the formulations were also submitted for tafamidis assay experiments, one sample was the supernatant of a centrifuged formulation and the other was a crude, un-centrifuged formulation, to determine the soluble fraction of tafamidis acid in each formulation.

Tafamidis assay. The solutions, standards, and samples used in the tafamidis assay analytical methods of the present disclosure were as described in Table 1.2.

TABLE 1.2

Tafamidis assay solutions and sample preparation

| | |
|---|---|
| Dilute phosphoric acid solution | 10 ml of orthophosphoric acid and 100 ml of water were weighed, transferred into a glass bottle, and mixed. |
| Buffer solution | 1.56 g of sodium dihydrogen phosphate dihydrate was weighed and transferred into a volumetric flask with 1000 ml of water. The pH was adjusted to 3.6 ± 0.05 with diluted phosphoric acid solution, mixed, filtered through a 0.45 μM membrane filter, and degassed. |
| Organic mixture | 500 ml each of acetonitrile and methanol were measured, transferred into a glass bottle, mixed, and degassed for 30 min. |
| Mobile phase | 350 ml of buffer solution and 650 ml of organic mixture were measured and transferred into a glass bottle, mixed, and degassed for 30 min. |
| Diluent solution | 600 ml of methanol and 400 ml of water were measured and transferred into a glass bottle, mixed for 30 minutes, and degassed. |
| Blank solution | 40 ml of tetrahydrofuran and 60 ml of diluent solution were measured and transferred into a 100 ml volumetric flask and mixed. 5 ml of the resulting solution was transferred into 100 ml volumetric flask with 95 ml of diluent solution. |
| Assay standard solution | 50 mg of tafamidis-fumaric acid co-crystal working standard was weighed and transferred into a 100 ml volumetric flask with 40 ml of tetrahydrofuran, sonicated until dissolved, brought to 100 ml with diluent solution, and mixed. 5.0 ml of the resulting solution was pipetted into a 100 ml of volumetric flask with 95 ml diluent solution, and mixed. Approximate tafamidis-fumaric acid co-crystal concentration: 0.025 mg/m. |
| Assay standard check solution | 50 mg of tafamidis-fumaric acid co-crystal working standard was weighed and transferred into a 100 ml volumetric flask with 40 ml of tetrahydrofuran, sonicated until dissolved, brought to 100 ml with diluent solution, and mixed. 5.0 ml of the resulting solution was pipetted into a 100 ml of volumetric flask with 95 ml diluent solution, and mixed. Approximate tafamidis-fumaric acid co-crystal concentration: 0.025 mg/ml. |
| Assay sample preparation | 50 mg of tafamidis-fumaric acid co-crystal sample was weighed and transferred into a 100 ml volumetric flask with 40 ml of tetrahydrofuran, sonicated until dissolved, brought to 100 ml with diluent solution, and mixed. 5.0 ml of the resulting solution was pipetted into a 100 ml volumetric flask with 95 ml diluent solution, and mixed. |

The chromatographic conditions for the tafamidis assay employed in the present disclosure were according to those set forth in Table 1.3.

TABLE 1.3

Tafamidis HPLC chromatographic parameters

| Chromatographic parameters | Equipment and/or conditions |
|---|---|
| System | HPLC equipped with variable wavelength and/or PDA (DAD) detector, column heater/chiller, and binary or a tertiary solvent pump |
| Column | Waters X-bridge C18, 50 mm × 4.6 mm, 3.5 µm |
| Column Temperature | 30° C. |
| Sample Tray Temperature | 25° C. |
| Detector Wavelength | UV 210 nm |
| Pump Mode | Isocratic |
| Flow Rate | 1.0 ml/min |
| Injection Volume | 20 µl |
| Tafamidis retention time | About 4.5 min |
| Run Time | 12 minutes |
| Needle Wash | Methanol: water (90:10) v/v |
| Column wash solutions | Acetonitrile: water = 10:90 v/v and followed by Acetonitrile: water = 90:10 v/v |

The HPLC system was equilibrated with mobile phase for about 30 minutes. Iterative injections of diluent were made until a clean and reproducible baseline was achieved. Record the chromatogram and identify any peak eluting at the retention time of major peaks. Five replicate injections of tafamidis-fumaric acid co-crystal working standard solution or tafamidis polymorph form 1 working standard solution were made and chromatograms recorded. The average and relative standard deviation (% RSD) for the tafamidis peak area responses were calculated from the five replicate injections of each tafamidis working standard solution.

Two replicate injections of standard check solution were made and chromatograms recorded. The average peak area responses of the tafamidis obtained from the two replicate injections of standard check solution were calculated and then the similarity factor was calculated. One injection of diluent was made before injecting each sample solutions. One injection of each sample solution was made, chromatogram recorded, and the tafamidis peak area determined. The Tafamidis concentration in the sample solution was calculated. After six injections of sample solution and at the end of the sequence, one injection of diluent was made followed by one injection of working standard solution (bracketing). The % RSD of tafamidis peak area obtained from the initial five injections of working standards and bracketing standard.

The equation employed to calculate percent assay for tafamidis in the samples of the formulations of the present disclosure are set forth in Table 1.4

TABLE 1.4

Tafamidis percent assay equation $$\% \text{ Assay} = \frac{Aspl}{Astd} \times \frac{Wstd}{100 \text{ mL}} \times \frac{5 \text{ mL}}{100 \text{ mL}} \times \frac{\% \ Pstd}{100\%} \times \frac{100 - Kf \ std}{100\%} \times \frac{100 \text{ mL}}{Wspl} \times \frac{100 \text{ mL}}{5 \text{ mL}} \times \frac{100}{\% \ Pspl} \times \frac{100\%}{100 - Kf \ spl} \times 100\%$$

Where:
| | |
|---|---|
| Astd | Average Peak Area of Tafamidis from first 5 replicate standards injections |
| Aspl | Peak Area of tafamidis from sample injection |
| Wstd | Weight of tafamidis used to prepare Standard |
| Wspl | Weight of tafamidis used to prepare Sample |
| % Pstd | Percentage purity of tafamidis-fumaric acid co-crystal or tafamidis polymorph form 1 in working standard |
| % Pspl | Percentage purity of tafamidis-fumaric acid co-crystal or tafamidis polymorph form 1 in sample |
| Kf std | % Water content of standard |
| Kf spl | % Water content of sample |

Aqueous tafamidis formulations 0263-13A, 0263-13B, 0263-13C, and 0263-13D comprised the ingredients and pH set forth in Table 1.5 and were also studied in the solubility and viscosity experimental protocols described in this Example 1.

TABLE 1.5

Tafamidis formulations 0263-13A-D

| | 0263-13A | | 0263-13B | | 0263-13C | | 0263-13D | |
|---|---|---|---|---|---|---|---|---|
| Ingredient | mg/ml | % w/v | mg/ml | % w/v | mg/ml | % w/v | mg/ml | % w/v |
| Tafamidis-fumaric acid co-crystal | 14.5* | 1.45 | 14.5* | 1.45 | 14.5* | 1.45 | 0 | 0 |
| Tafamidis form 1 | 0 | 0 | 0 | 0 | 0 | 0 | 12.2 | 1.22 |
| Purified water | 650 | 6.5 | 650 | 6.5 | 650 | 65 | 650 | 65 |
| Sodium carbonate | 8.3 | 0.83 | 8.3 | 0.83 | 8.3 | 0.83 | 8.3 | 0.83 |
| Povidone K 30 | 33.1 | 3.31 | 33.1 | 3.31 | 33.1 | 3.31 | 33.1 | 3.31 |

TABLE 1.5-continued

Tafamidis formulations 0263-13A-D

| | 0263-13A | | 0263-13B | | 0263-13C | | 0263-13D | |
|---|---|---|---|---|---|---|---|---|
| Ingredient | mg/ml | % w/v | mg/ml | % w/v | mg/ml | % w/v | mg/ml | % w/v |
| Polysorbate 20 | 112 | 11.2 | 112 | 11.2 | 112 | 11.2 | 112 | 11.2 |
| 1N HCl | Q.S. to pH 8.5 | | Q.S. to pH 8.5 | | Q.S. to pH 8.5 | | Q.S. to pH 8.5 | |
| Purified water | Q.S. | | Q.S. | | Q.S. | | Q.S. | |

*14.5 mg tafamidis-fumaric acid co-crystal is equivalent to 12.2 mg tafamidis + 2.3 mg fumaric acid.

Formulations 0263-13A, 0263-13B, 0263-13C, and 0263-13D were made as follows. A bulk master mix solution was made by mixing 16.25 g of purified water and 2.8 g of polysorbate 20 in a 25 ml beaker with a magnetic stir rod. 207.5 mg of sodium carbonate was then added and mixed until dissolved. 827.5 mg of povidone K30 was gradually added and mixed with the magnetic stir bar for at least twenty minutes until dissolved, clear, and free of bubbles Then 20.5 g of the bulk solution was weighed into a 25 ml scintillation vial and mixed with a magnetic stirring rod while being heated to 50° C. 181.25 mg of tafamidis-fumaric acid co-crystal or 152.5 mg of tafamidis polymorph 1 was slowly added and mixed while heating at 50° C. until a clear solution was formed. Then an additional 181.25 mg of tafamidis-fumaric acid co-crystal acid or 152.5 mg of tafamidis polymorph form 1 was slowly added with continued mixing at 50° C. until a clear solution was formed. The pH of resulting solutions was measured and adjusted to the pH indicated for each formulation in Table 1.2 using 1N HCl, and then diluted to 25 ml with purified water. Once a clear solution had formed, 5 ml was transferred into a microcentrifuge vial and centrifuged at 5000×g for 2 minutes. All visual solubility and viscosity observations for each of the formulations were then made and recorded. Two samples of each of the formulations were also submitted for tafamidis assay experiments, one sample was the supernatant of a centrifuged formulation and the other was a crude, un-centrifuged formulation, to determine the soluble fraction of tafamidis acid in each formulation.

The viscosity and solubility experimental results for formulation 0263-11A-D and 0263-13A-D are reported in Tables 1.6 and 1.7, respectively.

TABLE 1.6

Formulations 0263-11A-D

| | 0263-11A | 0263-11B | 0263-11C | 0263-11D |
|---|---|---|---|---|
| Visual observations | Cloudy hard gel, flowable after vigorous mixing | Opaque soft gel, flowable after mixing | Clear, flowable | Opaque soft gel, flowable after mixing |
| Label claim at 12.2 mg/ml | 92.4% | 97.8% | 99.5% | 97.3% |
| Assay | 11.19 mg/ml | 11.88 mg/ml | 12.07 mg/ml | 11.87 mg/ml |
| Soluble fraction | 8.30 mg/ml | 11.15 mg/ml | 12.02 mg/ml | 11.42 mg/ml |

TABLE 1.7

Formulations 0263-13A-D

| | 0263-13A | 0263-13B | 0263-13C | 0263-13D |
|---|---|---|---|---|
| Visual observations | Cloudy hard gel, flowable after vigorous mixing | Opaque soft gel, flowable after mixing | Clear, flowable | Opaque soft gel, flowable after mixing |
| Label claim at 12.2 mg/ml | 98.6% | 96.0% | 96.9% | 97.6% |
| Assay | 12.00 mg/ml | 11.69 mg/ml | 11.80 mg/ml | 11.88 mg/ml |
| Soluble fraction | 12.18 mg/ml | 11.54 mg/ml | 12.05 mg/ml | 11.95 mg/ml |

While the foregoing specification teaches the principles of the present invention, with examples provided for the purpose of illustration, it will be understood that the practice of the invention encompasses all variations, adaptations and/or modifications as come within the scope of the following claims and their equivalents.

What is claimed is:

1. A liquid pharmaceutical formulation, suitable for oral administration, comprising:
   an amount of tafamidis of from 0.5 mg/ml to 20 mg/ml;
   water;
   an amount of an alkaline pH modifier sufficient to yield a concentration of the tafamidis that is dissolved in the water of from 0.5 mg/ml to 19.8 mg/ml; and
   each of:
   (i) from 5 mg/ml to 50 mg/ml of a polyvinylpyrrolidone (PVP) of, wherein the PVP has a K value of from 10 to 120;
   (ii) from 50 mg/ml to 500 mg/ml of a polysorbate 20, a polysorbate 40, a polysorbate 60, a polysorbate 80, or a combination thereof of; and
   (iii) an amount of an acidic pH adjuster sufficient to yield, in combination with the alkaline pH modifier, a pH of the formulation of from 6 to 11
   wherein the formulation has a pH of from 6 to 11; and
   wherein the alkaline pH modifier is sodium carbonate, potassium carbonate, calcium carbonate, magnesium carbonate, ammonium carbonate, sodium bicarbonate, potassium bicarbonate, calcium bicarbonate, magnesium bicarbonate, ammonium bicarbonate, sodium citrate, potassium citrate, calcium citrate, sodium hydroxide, potassium hydroxide, calcium hydroxide, magnesium hydroxide, ammonium hydroxide, sodium phosphate, potassium phosphate, calcium phosphate, magnesium phosphate, sodium oxide, potassium oxide, calcium oxide, magnesium oxide, ammonium phosphate, ammonia, tromethamine, or a combination of at least any two thereof.

2. The formulation of claim 1, wherein the PVP is PVP K30 and wherein the polysorbate is the polysorbate 20.

3. The formulation of claim 1, wherein the PVP is PVP K90 and wherein the polysorbate is the polysorbate 20.

4. The formulation of claim 1, wherein the PVP is PVP K90 and wherein the polysorbate is the polysorbate 20.

5. The formulation of claim 2, wherein the alkaline pH modifier is the sodium carbonate, the sodium hydroxide, the potassium hydroxide, the tromethamine or a combination of at least any two thereof and wherein the acidic pH adjuster is hydrochloric acid, hydrofluoric acid, sulfuric acid, chromic acid, nitric, and phosphoric acid, or a combination of at least any two thereof.

6. The formulation of claim 3, wherein the alkaline pH modifier is the sodium carbonate, the sodium hydroxide, the potassium hydroxide, the tromethamine, or a combination of at least any two thereof and wherein the acidic pH adjuster is hydrochloric acid, hydrofluoric acid, sulfuric acid, chromic acid, nitric, and phosphoric acid, or a combination of at least any two thereof.

7. The formulation of claim 4, wherein the alkaline pH modifier is the sodium carbonate, the sodium hydroxide, the potassium hydroxide, the tromethamine, or a combination of at least any two thereof and wherein the acidic pH adjuster is hydrochloric acid, hydrofluoric acid, sulfuric acid, chromic acid, nitric, and phosphoric acid, or a combination of at least any two thereof.

8. The formulation of claim 5, wherein the content of the tafamidis that is dissolved in the water is from 5 mg/ml to 15 mg/ml.

9. The formulation of claim 6, wherein the content of the tafamidis that is dissolved in the water is from 5 mg/ml to 15 mg/ml.

10. The formulation of claim 7, wherein the content of the tafamidis that is dissolved in the water is from 5 mg/ml to 15 mg/ml.

11. The formulation of claim 10, wherein the formulation is free of added polyethylene glycol and wherein the formulation is free of added glycerol.

12. A method of treating cardiomyopathy or peripheral neuropathy arising from transthyretin amyloidosis, comprising orally administering the formulation of claim 1 to a subject presenting cardiomyopathy or peripheral neuropathy arising from transthyretin amyloidosis.

13. The method of claim 12, wherein the formulation is administered to the subject once daily and wherein the formulation comprises from 10 mg to 80 mg tafamidis.

14. A liquid pharmaceutical formulation, suitable for oral administration, that comprises:
   from 10 mg/ml to 15 mg/ml of a tafamidis;
   water;
   an amount of an alkaline pH modifier that is from 5 mg/ml to 10 mg/ml and that is sufficient to yield a content of the tafamidis that is dissolved in the water of from 10 mg/ml to 12.5 mg/ml, wherein the alkaline pH modifier is sodium carbonate, sodium hydroxide, potassium hydroxide, tromethamine, or a combination thereof;
   from 30 mg/ml to 35 mg/ml of a PVP K30;
   from 10 mg/ml to 15 mg/ml of a polysorbate 20; and
   an amount of an acidic pH adjuster that, in combination with the alkaline pH modifier, is sufficient to adjust the pH of the formulation to from about pH 6 to about pH 10, wherein the acidic pH adjuster is hydrochloric acid, hydrofluoric acid, sulfuric acid, chromic acid, nitric, and phosphoric acid, or a combination of at least any two thereof.

15. The formulation of claim 14, wherein the formulation is free of both: (i) added polyethylene glycol, and (ii) glycerol.

16. A liquid pharmaceutical formulation, suitable for oral administration, that comprises:
   about 12.2 mg/ml of a tafamidis;
   about 8.3 mg/ml of a sodium carbonate;
   about 33.1 mg/ml of a PVP K30;
   about 11.2 mg/ml of a polysorbate 20;
   an amount of hydrochloric acid sufficient to adjust the pH of the formulation to from about pH 6 to about pH 10; and
   water,
   wherein a percentage of the tafamidis in the formulation dissolved in the water is from about 75% to about 99%.

* * * * *